United States Patent [19]

Schachar et al.

[11] 4,298,004
[45] Nov. 3, 1981

[54] SURGICAL METHOD FOR ALTERING THE CURVATURE OF THE CORNEA OF RABBITS

[76] Inventors: Ronald A. Schachar, 213 N. Barrett, Denison, Tex. 75020; Norman S. Levy, 2218 NW. 29th St., Gainesville, Fla. 32605

[21] Appl. No.: 15,656

[22] Filed: Feb. 27, 1979

[51] Int. Cl.³ .................... A61F 17/32; A61F 1/16
[52] U.S. Cl. .......................... 128/305; 3/13; 3/36; 128/1 R; 128/DIG. 8
[58] Field of Search ......... 3/13, 36; 128/1 R, DIG. 8, 128/20, 305; 83/915.5; 260/112 P

[56] References Cited

U.S. PATENT DOCUMENTS

| | | | |
|---|---|---|---|
| 1,245,983 | 11/1917 | Satow | 260/112 R |
| 3,776,230 | 12/1973 | Neete | 3/13 |
| 3,945,054 | 3/1976 | Federov et al. | 3/13 |
| 4,002,169 | 1/1977 | Cupler | 128/276 |
| 4,180,075 | 12/1979 | Marinoff | 128/305 |

FOREIGN PATENT DOCUMENTS 772569  4/1957  United Kingdom ............ 3/13

OTHER PUBLICATIONS

"A Lens for All Seasons", Tennant, Aug. 1976, p. 46.
Keratoprosthesis–American Journal of Ophthalmology, vol. 54, No. 2, Aug. 1962, pp. 284-294.
Medical Section–Collagen Currents, Ethicon, Inc., Sommerville, N. J., vol. 5, No. 1, Jul. 1964, pp. 25-26.

*Primary Examiner*—Robert W. Michell
*Assistant Examiner*—J. L. Kruter
*Attorney, Agent, or Firm*—Richards, Harris & Medlock

[57] ABSTRACT

A method for altering the radius of curvature of the cornea together with an apparatus for use therein is provided. Apparatus (10) includes a circular ring (12) which can be placed over the eye for concentrically surrounding the cornea. Blade (14) which forms a part of apparatus (10) is mounted for retractable movement to and away from the cornea. Blade (14) is also able to rotate through a limited arc so that a sector-shaped incision (46) can be made in the cornea. Collagen or any other suitable material (50) is injected into sector-shaped incision (46) to alter the radius of curvature of the cornea.

11 Claims, 6 Drawing Figures

SURGICAL METHOD FOR ALTERING THE CURVATURE OF THE CORNEA OF RABBITS

TECHNICAL FIELD

This invention relates to correcting vision defects and more particularly to changing the radius of curvature of the cornea.

BACKGROUND ART

Ophthalmologists have long been concerned with correcting hyperopia in the eye and defects which relate to the curvature of the cornea. Well-known methods of correcting hyperopia include corrective lenses, such as eye glasses or contact lenses. These methods have obvious drawbacks as they do not form an integral part of the eye structure. Eye glasses and contact lenses are often bothersome to wear and are subject to loss or breakage. Contact lenses also present additional problems such as eye infections and corneal damage related to excessive abrasion or scratching.

A need therefore exists for a method and apparatus for correcting hyperopia without external corrective lenses. Further, a need also exists for the correction of hyperopia wherein the radius of curvature of the cornea is permanently altered.

DISCLOSURE OF THE INVENTION

In accordance with the present invention, a method is provided for performing an operation on the cornea which decreases the cornea's radius of curvature, together with an apparatus for use in accordance with the method. The apparatus according to the invention includes a small double-edged surgical blade mounted on a structure secured to a circular ring. The circular ring is adapted to be placed in position over an eye for concentrically surrounding the cornea of the eye so that the blade may be positioned and oriented with respect to the cornea. The blade is slidably mounted for longitudinal movement of the blade normal to the ring in a plane which is perpendicular to the longitudinal axis of the ring. When the apparatus is placed in position over an eye, the blade is movable from a first position in which the blade does not contact the cornea to a second position in which the blade penetrates a portion of the cornea in a position normal to the ring. In the second position, the blade can be pivoted through a limited arc on either side of the second position to form a sector-shaped incision in the cornea. The vertical distance between the blade and the ring can be adjusted for penetrating the cornea with the knife at a predetermined corneal depth.

After the sector-shaped incision has been made, the knife is removed from the cornea and the circular ring is lifted off of the eye. An injection of specially prepared collagen is made into the sector-shaped incision at the point where the knife was inserted into the cornea. The collagen is non-antigenic so that the body will not react to the collagen. While the collagen is being injected into the sector-shaped incision, a keratometer monitors the change in the cornea's radius of curvature and the injection of collagen is terminated when the radius of curvature reaches the desired value.

BRIEF DESCRIPTION OF THE DRAWINGS

A more complete understanding of the invention and its advantages will be apparent from the following Detailed Description taken in conjunction with the accompanying drawings in which.

DETAILED DESCRIPTION

Figure 1:
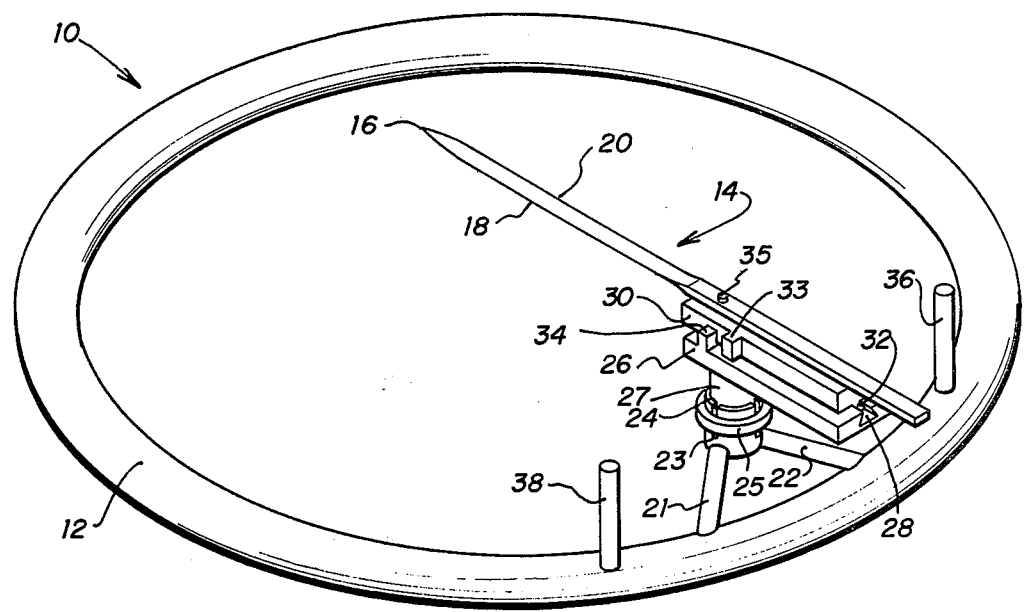
FIG. 1 is a perspective view of the apparatus according to the invention.

FIG. 1 illustrates in perspective view the apparatus according to the invention which is used to make a sector-shaped incision in the cornea and is generally indicated by 10. Circular ring 12 is preferably toroidal and dimensioned so that its interior diameter is slightly larger than the diameter of a human cornea. Circular ring 12 acts as the frame for apparatus 10 and abuts the surface of the eye to permit the proper orientation of apparatus 10 with respect to the cornea during operation of the apparatus.

A blade 14 is carried by ring 12 and has three cutting edges illustrated in FIG. 1 as first cutting edge 16, second cutting edge 18 and third cutting edge 20. First cutting edge 16 forms the sharpened point of blade 14. Preferably, blade 14 is narrow relative to the thickness of the cornea.

First support member 21 and second support member 22 are attached to circular ring 12 and angle inwardly and upwardly from circular ring 12 for securing support structure 23. Support structure 23 comprises a hollow cylinder having a plurality of spaced apart longitudinal slots 24 cut therethrough as shown in FIG. 1. A tightening ring 25 is dimensioned to fit over support structure 23 as hereinafter described. A platform 26 includes a cylindrical finger 27 which projects downwardly therefrom. Cylindrical finger 27 is dimensioned to allow insertion into and frictional engagement with support structure 23. Once cylindrical finger 27 is inserted to the desired position, tightening ring 25 can be moved downwardly to lock cylindrical finger 27 in support structure 23. The inner diameter of tightening ring 25 is slightly less than the outer diameter of support structure 23. Thus, when tightening ring 25 is moved downwardly over that portion of support structure 23 that contains longitudinal slots 24, support structure 23 will frictionally grip cylindrical finger 27 in a stationary position. In this manner, the height of blade 14 relative to the cornea can be adjusted.

Figures 2, 3:
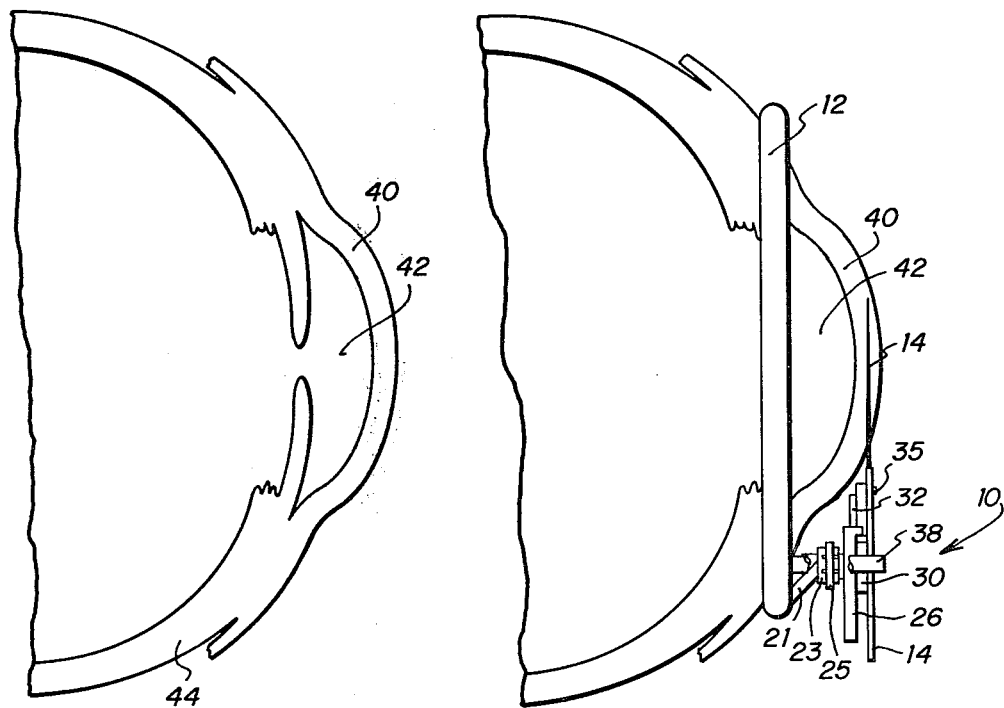
FIG. 2 is a horizontal section through an eyeball partially broken away.
FIG. 3 is a horizontal section of an eyeball illustrating the initial incision into the cornea according to the method of the invention.

Platform 26 contains therein a groove 28 which extends longitudinally of platform 26 and normal the circumference of circular ring 12. Blade 14 is pivotally mounted at pivot point 35 on a movable platform 30 which is slidably mounted on platform 26 by a tongue 32 which forms an integral part of movable platform 30 and slidably fits within groove 28. Thus, platform 30 and blade 14 are longitudinally movable perpendicular to the longitudinal axis of circular ring 12. When ring 12 is placed in position over an eye, as shown in FIG. 3, blade 14 may be moved from a first position in which blade 14 will not be in contact with the cornea, to a second position in which blade 14 penetrates a portion of the cornea over a predetermined length. The penetration of blade 14 is controlled by the length of blade 14 and also by two bosses 33 located on either side of movable platform 30 and complementary bosses 34 located on platform 27. Bosses 33 and 34 thus prevent further longitudinal movement of blade 14 and movable platform 30 towards the center of circular ring 12.

Blade 14 is capable of limited rotation about pivot point 35 in a plane parallel to the plane which extends through the circumference of circular ring 12. Rotation of blade 14 is limited by a first stop 36 and a second stop 38 mounted on circular ring 12. Apparatus 10 can be adjustable (not shown) for positioning first stop 36 and second stop 38 at varying distances from each other along circular ring 12, thereby determining and restricting rotation of blade 14 through a limited arc so that blade 14 sweeps out a sector-shaped area in which the radius of the sector is determined by the distance from pivot point 35 to the tip of blade 14.

The effective length of second cutting edge 18 and third cutting edge 20 depends on the radius of the second-shaped incision that is desired. Preferably, the incision will extend over the central part of the cornea and the radius of the sector-shaped incision will generally be from about 4 millimeters to about 8 millimeters. The actual incision in the cornea will not be a perfect sector, since the apex of the sector is pivot point 35 which is located exteriorly of the cornea when the incision is made. For purposes of the disclosure, however, the incision made by the present apparatus will be termed sector-shaped.

The total length of blade 14 is such that when blade 14 is moved to the second position and rotated about pivot point 35, the end of blade 14 opposite the tip of blade 14 extends past circular ring 12 so that end of blade 14 can make contact with stops 36 and 38 to prevent rotation of blade 14 past a predetermined point. In an alternate embodiment, the blade may be curved to approximate the curvature of the cornea. The platform to which the blade is mounted could also be movable through an arc which is essentially of the same curvature as the blade so that the curved blade can be inserted into the cornea. In this embodiment it would be necessary to provide pivoting of the curved blade in a curved plane once the blade is inserted in position in the cornea. The circular ring structure would not have to be altered.

According to the method of the present invention, the radius of curvature of the cornea is decreased, thereby increasing the dioptric power of the cornea. FIG. 2 is a diagramatic horizontal section through a human eyeball partially broken away. As is well-known, the eyball includes a cornea 40 which contains aqueous humor 42. A sclera 44 is the tough white supporting tunic of the eyeball and covers the entire eyeball except for corena 40.

FIGS. 3–6 illustrate various sequential steps and the results obtained using the method and apparatus of the invention. As shown in FIG. 3, a horizontal section of an eyeball is illustrated with apparatus 10 in place and resting on sclera 44. Apparatus 10 is positioned so that circular ring 12 is concentric with cornea 40. Preferably, apparatus 10 is positioned so that the incision can be made from the temple side of cornea 40. This facilitates the making of the incision and subsequent procedures because a greater area for movement and access to the cornea is provided. Blade 14 is positioned away from cornea 40 in the first position previously referred to during the initial placement (not shown) of apparatus 10 on sclera 44. FIG. 3 illustrates the initial incision into cornea 40 in which blade 14 moves towards cornea 40 along a line normal to circular ring 12 and penetrates the cornea at a predetermined depth, blade 14 being inserted a predetermined distance into cornea 40. Preferably, the incision is approximately from midway to one-third through the depth of cornea 40 measured from the exterior surface and extends over the central part of cornea 40. In one embodiment in accordance with the present invention, the sector-shaped incision is essentially parallel to the surface of the cornea in a single plane.

After the initial incision into cornea 40, blade 14 is rotated through a limited arc, determined by the position of first stop 36 and second stop 38 thereby making a sector-shaped incision 46 in cornea 40. Since pivot point 34 is relatively close to the point at which the surface of cornea 40 is penetrated by blade 14, a relatively small part of the incision extends through the exterior of cornea 40, since the apex of the sector is approximately the point where blade 14 first penetrates cornea 40. The advantages of the resulting small opening will be hereinafter described.

Figure 4:
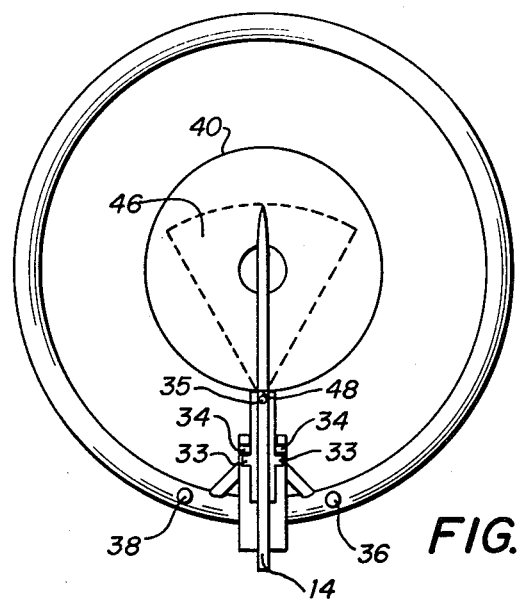
FIG. 4 is a frontal view of an eyeball showing the completed incision.

FIG. 4 is a frontal view of a eyeball which shows the completed incision into cornea 40 with blade 14 of apparatus 10 in a retracted position, away from cornea 40. Since movement of the blade 14 is in a single plane, the resulting incision is also planar.

After the incision has been completed, apparatus 10 is removed from the eyeball. An injection of inert, non-antigenic transparent material 50 is then made into sector-shaped incision 46 of cornea 40 through opening 48. Preferably, material 50 which is injected into the incision is a specially prepared collagen. Collagen is an albuminoid which is the main supportive protein of connective tissue. Collagen for use according to the invention may be obtained from several sources. For example, non-antigenic collagen may be obtained from postmortum eyes. Collagen may also be obtained from the Sigma Chemical Corporation in an unpurified form. This type of collagen must be purified before it can be used in accordance with the invention. For example, the collagen can be refined by ultracentrifugation, by gel electrophoresis or any other methods known to those skilled in the art. After purification, the collagen can be made non-antigenic by either denaturing the collagen within acidic or alkaline solution or by heating. For use in accordance with the invention, after purification and denaturing, the collagen must be essentially transparent.

Figures 5, 6:
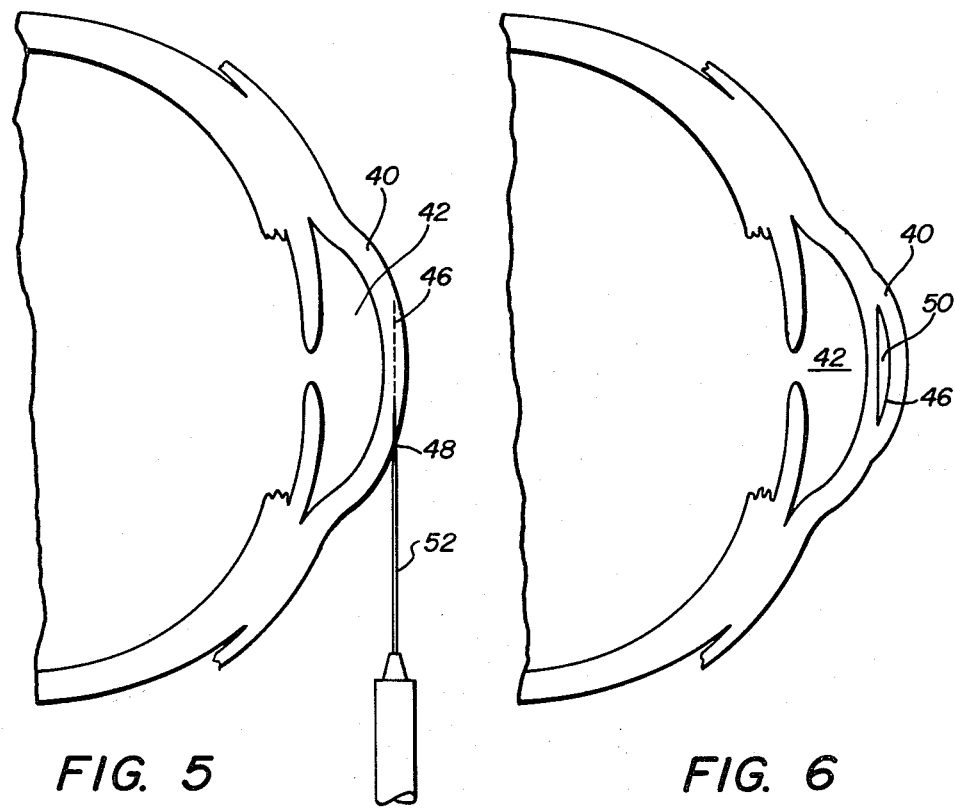
FIG. 5 is a horizontal section through an eyeball, partially broken away, illustrating injection of collagen into the incision.
FIG. 6 is a horizontal section through an eyeball, partially broken away, illustrating the change in the curvature of the cornea resulting from the method according to the invention.

After processing the collagen, it is ready for injection into sector-shaped incision 46. To facilitate the injection of the collagen into incision 46, the collagen is heated to a fluid state and injected into sector-shaped incision 46 by injecting it through needle 52 which has been inserted through opening 48 as shown in FIG. 5. As the injection of the collagen into sector-shaped incision 46 proceeds, the radius of curvature of cornea 40 is decreased. During the injection process the radius of curvature of cornea 40 may be monitored through the use of a keratometer. After the desired radius of curvature has been obtained, the injection process is terminated and the needle is withdrawn from opening 48 of sector-shaped incision 46. After the collagen reaches body temperature, it forms a gel. Injection of non-antigenic material 50 causes sector-shaped incision 46 to be transformed into a pocket which approaches a circular shape. Since opening 48 at the injection site of blade 14 is relatively small, usually there will be no need for a suture to close opening 48.

FIG. 6 illustrates the eyeball and cornea 40 after the operation has been completed and the radius of curvature of cornea 40 decreased showing the inert, non-antigenic transparent material 50 in incision 46.

The injection can be repeated numerous times and it is also possible to remove the collagen or material 50 after being injected, if for example, too much collagen was injected into the cornea.

While the invention has been described with reference to the preferred embodiments, it is to be understood that various other modifications of this invention may be made and will now be apparent to those skilled in the art and such modifications are intended to be within the scope of the appended claims.

We claim:

1. A method for decreasing the radius of curvature of a cornea comprising:
    forming an incision in the cornea that extends over the central portion of the cornea, said incision including a relatively small opening that extends through the surface of the cornea; and
    introducing a heated inert, non-antigenic transparent fluid material into said incision to decrease the radius of curvature of the cornea, said inert, non-antigenic transparent fluid material being of the type that is a gel at body temperature after cooling.

2. The method as recited in claim 1 wherein said incision is made at a depth from the surface of the cornea of approximately one-third to approximately one-half the depth of the cornea.

3. The method as recited in claim 1 wherein said incision has a sector-shaped, the apex of said sector-shaped incision being located in the temple side of the cornea.

4. The method as recited in claim 1 wherein said inert non-antigenic transparent material is collagen.

5. The method as recited in claim 4 wherein said collagen is purified by ultracentrifugation and denatured.

6. The method as recited in claim 1 wherein the shape of said incision is that of a sector, the apex of said sector penetrating the exterior surface of the cornea.

7. The method as recited in claim 1 further comprising
    monitoring the radius of curvature while introducing said material; and
    terminating the introduction of said material when the desired radius of curvature is attained.

8. A method of altering a cornea to a predetermined, decreased radius of curvature comprising:
    forming a sector-shaped incision in the cornea, said sector-shaped incision being over the central part of the cornea with essentially only the apex of said incision penetrating through a surface of the cornea;
    injecting a heated, inert, non-antigenic transparent fluid material into said incision, said non-antigenic transparent fluid being of the type that is a gel at body temperature after cooling;
    monitoring the radius of curvature of the cornea while injecting said material into said incision; and
    stopping the injection of said material into said incision when the desired decreased radius of curvature is obtained.

9. The method as recited in claim 8 wherein the radius of curvature of the cornea is monitored with a keratometer.

10. The method as recited in claim 8 wherein said sector-shaped incision is essentially parallel to the surface of the cornea in a single plane.

11. The method as recited in claim 8 wherein said sector-shaped incision is in a curved plane.

* * * * *

UNITED STATES PATENT AND TRADEMARK OFFICE
CERTIFICATE OF CORRECTION

PATENT NO. : 4,298,004

DATED : November 3, 1981

INVENTOR(S) : Ronald A. Schachar and Norman S. Levy

It is certified that error appears in the above-identified patent and that said Letters Patent are hereby corrected as shown below:

Col. 3, line 24-25, "second-shaped" should be --sector-shaped--

Col. 5, line 37, "sector-shaped" should be --sector-shape--.
line 38, "in" should be --on--.

Signed and Sealed this

Sixteenth Day of March 1982

[SEAL]

Attest:

Attesting Officer

GERALD J. MOSSINGHOFF

Commissioner of Patents and Trademarks